(12) United States Patent
Walton

(10) Patent No.: US 7,157,919 B1
(45) Date of Patent: Jan. 2, 2007

(54) METHOD AND SYSTEM FOR DETECTING SOOT AND ASH CONCENTRATIONS IN A FILTER

(75) Inventor: Frank B Walton, Pinawa (CA)

(73) Assignee: Caterpillar inc., Peoria, IL (US)

( * ) Notice: Subject to any disclaimer, the term of this patent is extended or adjusted under 35 U.S.C. 154(b) by 0 days.

(21) Appl. No.: 11/189,530

(22) Filed: Jul. 26, 2005

(51) Int. Cl.
*G01R 27/32* (2006.01)

(52) U.S. Cl. ...................... 324/641; 324/639

(58) Field of Classification Search ............... 324/639, 324/698, 641
See application file for complete search history.

(56) References Cited

U.S. PATENT DOCUMENTS

| | | | |
|---|---|---|---|
| 3,913,012 A * | 10/1975 | Kujath | ......................... 324/640 |
| 4,477,771 A | 10/1984 | Nagy et al. | |
| 4,825,651 A | 5/1989 | Puschner et al. | |
| 4,979,364 A | 12/1990 | Fleck | |
| 5,074,112 A | 12/1991 | Walton et al. | |
| 5,157,340 A | 10/1992 | Walton et al. | |
| 5,177,444 A * | 1/1993 | Cutmore | ...................... 324/637 |
| 5,195,317 A | 3/1993 | Nobue et al. | |
| 5,279,146 A * | 1/1994 | Asano et al. | ............... 73/28.04 |
| 5,423,180 A | 6/1995 | Nobue et al. | |
| 5,497,099 A | 3/1996 | Walton | |

FOREIGN PATENT DOCUMENTS

WO    WO 93/05388    *   3/1993

* cited by examiner

*Primary Examiner*—Walter Benson
(74) *Attorney, Agent, or Firm*—Michael L. Woods

(57) ABSTRACT

A system and method for detecting soot and or ash loading within a filter is provided. The method comprises the steps of transmitting a source RF signal through a filter, measuring a reflected RF signal, measuring a transmitted RF signal, calculating reflected power by comparing the source RF signal with the reflected RF signal, calculating attenuated power by comparing the source RF signal with the transmitted RF signal, and determining soot loading based on reflected power and transmitted power. The system and method may also determine ash loading.

23 Claims, 3 Drawing Sheets

METHOD AND SYSTEM FOR DETECTING SOOT AND ASH CONCENTRATIONS IN A FILTER

TECHNICAL FIELD

This invention relates generally to a radio frequency ("RF") sensor, system, and method for detecting and measuring soot and or ash loading in a particulate trap, such as a ceramic diesel particulate filter.

BACKGROUND

In order to meet stringent exhaust emission regulations, some engine manufacturers have installed exhaust aftertreatment systems comprising, in part, of particulate traps ("filters"). These filters collect soot—a mixture of carbon particulates and condensed organic material—and any inorganic particulates ("ash"), which are produced primarily as a result of the combustion of small amounts of engine lubricating oil. The concentration of the soot collected in the filter is constantly monitored for the purpose of signaling to the engine controller when regeneration, or cleaning, of the filter is necessary. Regeneration of the filter is necessary in order to reduce the exhaust backpressure to the engine and to protect the filter from damage.

All filter regeneration strategies involve some sort of soot oxidation process that must be carefully managed in order to avoid thermal damage to the filter. In particular, the carbon particulates contain the highest calorific content and, as a result, carbon particulates release the highest amount of energy within the filter during the regeneration process. Therefore, it is essential to accurately assess the carbon particulate concentration within the filter prior to initiating the filter regeneration process.

To date, one of the primary methods for assessing soot accumulation within the filter has been to measure the pressure drop across the filter. Due to the large number of engine operating parameters that effect engine exhaust flow rates—and thus pressure drop across a filter—any correlation between pressure drop and soot concentration may not accurately determine particulate trap loading. The resistance-to-flow by soot is also a function of the ratio of the carbon particulates to condensed organic concentrations—the condensed organic material is often referred to as the soluble organic fraction ("SOF")—which is difficult if not impossible to determine by pressure drop measurements. Similarly, some engine manufacturers have found it difficult to differentiate between accumulated soot and ash in a filter by pressure drop across a filter.

This application discloses, among other things, a system that uses an RF-based measurement method to directly measure carbon particulate concentrations within the filter. After filter regeneration, the method can also be used to measure ash build up within the filter.

To those knowledgeable in the art, it is well known that the transmission of an RF signal through a non-magnetic medium is effected by its complex permittivity. The real component is called the dielectric constant and the imaginary component is called the loss factor. The dielectric constant affects the space velocity of an RF signal and loss factor is essentially a resistive component that converts RF energy to heat. The permittivity of a medium is a function of its atomic structure and density, and can vary with temperature and RF frequency. Differences in the permittivity of materials form the underlying basis for RF-based measurement methods.

Ceramic filters, made of materials such as cordierite or alumina, are largely transparent to RF energy. That is, these latter ceramic materials have a very low loss factor. In contrast, carbon particulates have a relatively high loss factor and are hence a good absorber of RF energy. The accumulation of carbon particulates effectively alters the apparent permittivity of a ceramic filter. U.S. Pat. No. 5,497,099 to Frank Walton ("'099") discloses that it is possible to monitor the level of soot accumulation on a diesel engine filter medium by detecting changes in the effective permittivity of the ceramic filter medium As further disclosed in '099, an antenna system comprising of parallel transmitting and receiving antennae is inserted parallel to the central axis of the cylindrical metal filter cavity and is inductively coupled in a direction radial to the antennae and filter axis. These antennae may be inserted in either opposite ends of the filter or within the same end of the filter. It can be readily demonstrated that the measurement volume is axially confined to the area of overlap of the antennae and in the radial direction by the metal walls of the metal filter housing. Each antenna may consist of one or more metallic elements. The addition of more than one element to an antenna may be in some applications to improve the broadband frequency transmission and reception characteristics of the antenna system. An amplitude modulated RF source sends a signal to a splitter. The splitter applies the signal to both the transmitting antenna (20) and to a detector. This latter detector produces a reference output signal that is representative of the power of the signal prior to transmission to the transmitting antenna (20).

Further referencing '099, a second detector is provided, which is electrically connected to the receiving antenna, and which produces an output signal representative of the power transmitted through the filter medium. The first and second detector output signals are applied to a comparator that produces an output signal, which is proportional to the difference in the signal strength of the transmitted and received signals. Accordingly, the transmission loss through the filter medium, which, in turn, is representative of the change in the effective loss factor caused by accumulation of soot within the filter. That is when there is little or no accumulation of soot in the filter there will only be a small transmission loss in the signal strength. As the soot accumulation increases, the difference in signal strength between the transmitted and received increases. The comparator can be designed to provide a variable output that is a function of the soot accumulation within the filter medium or to indicate when a certain predetermined soot level is reached, or both.

'099 further provides that the power source is arranged to emit RF energy over range of frequencies with the preferred frequency band being up to one octave, i.e., a 2 to 1 range in frequency. The signal is averaged over a preferred bandwidth.

'099, however, fails to differentiate between the relative concentrations of carbon particulates and SOF. High levels of SOF interfere with the ability of the RF sensor system to accurately assess the carbon particulate concentrations within a filter. The system disclosed in '099 fails to provide sufficient RF measurement parameters to differentiate between variable concentrations of carbon particulates and SOF. The system disclosed in '099 also fails to provide a method for assessing ash accumulation within the filter medium.

The system of the present disclosure measures both transmitted and reflected RF power over a range of discrete frequencies. In effect, the RF spectral response can be shown to uniquely characterize both the quantity and the composition of the soot, i.e., the ratio of the carbon particulates to the SOF. This additional RF spectral information can be used to develop correlations.

In addition to being able to determine the accumulation of soot in a filter, the disclosed system provides for a method of determining the accumulation of ash in the filter. Measurements of the complex permittivity of ash indicate that the loss factor is very low under the temperature conditions where soot is being filtered from diesel exhaust. That is, it does not interfere with the ability to detect soot accumulation. However, at temperatures at or above where soot oxidation occurs, the loss factor increases with increasing temperature. Hence after the soot has been removed by oxidation and the filter remains at regeneration temperatures, the effective permittivity of the filter reflects the thermally enhanced permittivity of the ash. It is, therefore, possible by development correlations to determine the accumulation of ash within the filter. As with the determination of soot, both reflected and transmitted power measurements over a range of frequencies can be used to develop these latter correlations.

SUMMARY

The reader should understand that both the foregoing general description and the following detailed description are exemplary and explanatory only and are not restrictive of the invention.

In one embodiment, a method for detecting soot and or ash loading within a filter is provided. In this embodiment, the method comprises the steps of transmitting a source RF signal through a filter, measuring a reflected RF signal, measuring a transmitted RF signal, calculating reflected power by comparing the source RF signal with the reflected RF signal, calculating attenuated power by comparing the source RF signal with the transmitted RF signal, and determining soot loading based on reflected power and transmitted power.

In this particular embodiment, the method may further be characterized in that the source RF signal is transmitted over a range of frequencies. For example, the range of frequencies may be from about 200 MHz to about 400 MHz. The reader should appreciate, however, that any range of frequencies may be used.

This embodiment may also further comprise the step of determining the ratio of carbon particulates to condensed organic material and or may further comprise the step of determining carbon particulate loading.

In addition, this embodiment may also further comprise the step of determining the ash loading.

In another embodiment, a system for measuring soot loading within a filter is provided. This system may comprise a transmitting antenna configured to transmit a range of radio frequencies across the filter, a receiving antenna configured to receive a range of radio frequencies across the filter, a first detector configured to receive and send a reference signal, a second detector configured to receive and send a reflected signal, a third detector configured to receive and send a transmitted signal, a first comparator configured to compare the reference signal with the reflected signal, and a second comparator configured to compare the reference signal with the transmitted signal.

In this system embodiment, the system may be characterized in that the transmitting antenna is substantially parallel to the receiving antenna. Further, the transmitting antenna and or receiving antenna may be imbedded in the filter. Additionally, the transmitting antenna may be configured to transmit a radio frequency in the range of 200–400 MHz. In one particular embodiment, the transmitting antenna and or receiving antenna may be substantially parallel to the axis of the filter.

In this system embodiment, the system may comprise a housing, which may or may not be configured to shield the receiving antenna and transmitting antenna from RF noise. The system may also comprise a signal processor configured to calculate carbon particulate loading in the filter based on outputs from the first comparator and second comparator. Additionally, the system controller may be configured to calculate the ratio of carbon particulates to condensed organic material based on outputs from the first comparator and second comparator and, likewise to calculate the accumulation of ash.

In yet another embodiment, a method of controlling regeneration across a filter is provided. This method may comprise the steps of transmitting a radio frequency across a filter, measuring a reflected signal, measuring an attenuated signal, and generating a signal for filter regeneration based on the reflected and the transmitted power signals.

In this particular embodiment, the radio frequency may be variable across a frequency range. Further, the frequency may vary from within about 200–400 MHz. The method may further comprise the step of determining the ratio of carbon particulates to condensed organic material. Additionally and or alternatively, the method may further comprise the step of determining carbon particulate loading and or ash loading

BRIEF DESCRIPTION OF THE DRAWINGS

The accompanying drawings, which are incorporated in and constitute a part of this specification, illustrate several exemplary embodiments of the invention and, together with the description, serve to explain the principles of the invention. In the drawings.

DETAILED DESCRIPTION

Figure 1:
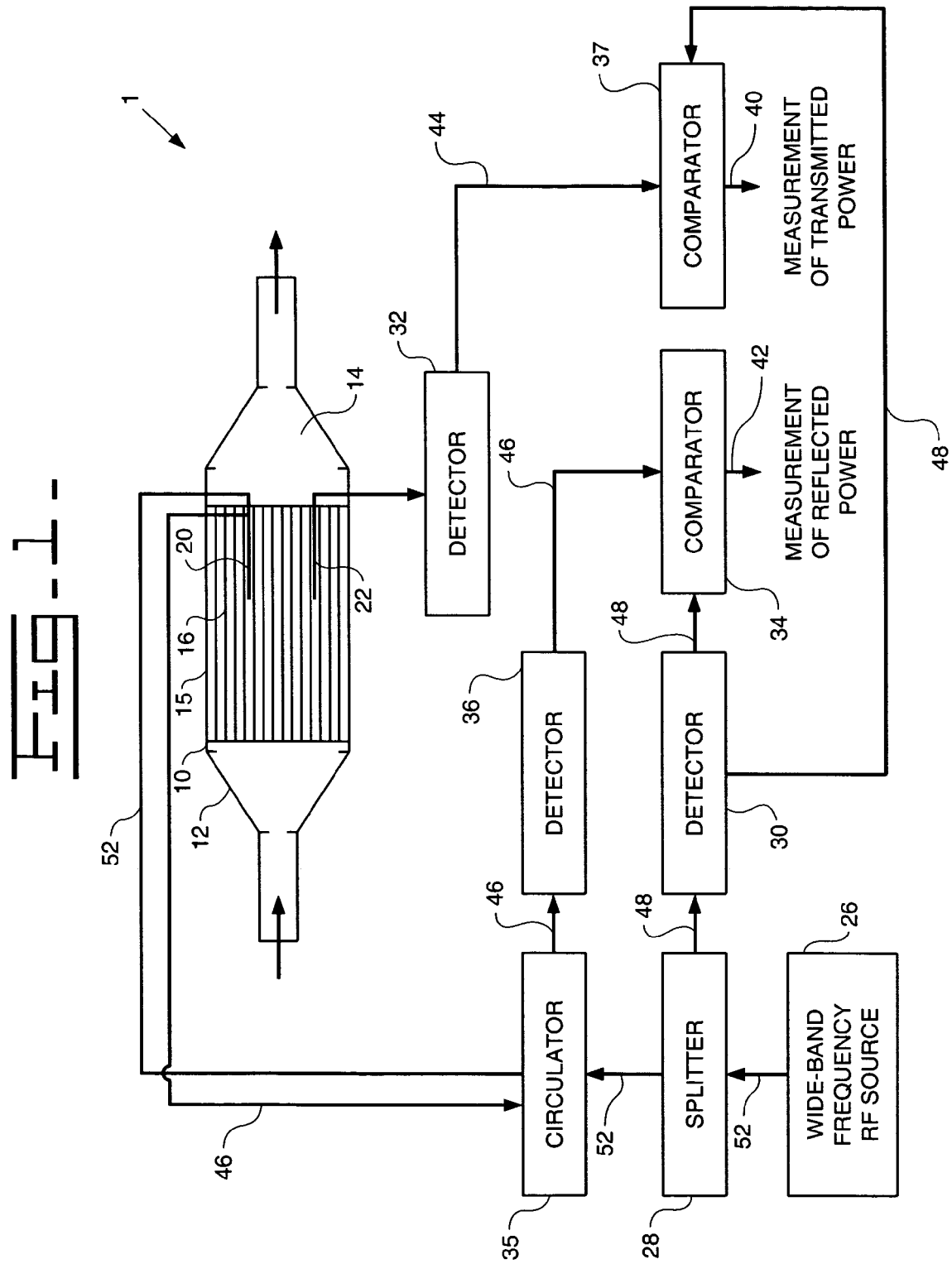
FIG. 1 is a block diagram of an embodiment of the system that is used to measure particulate trap loading.

FIG. 1 discloses a system 1 configured to measure soot and or ash loading within a filter 16 of an engine exhaust system. System 1 comprises a filter housing 10 having an inlet end section 12 and outlet end section 14, both of which are adapted to be connected to engine exhaust pipes in a manner well known in the art. Housing 10 comprises a chamber 15 configured to receive a filter element 16 of suitable construction. A transmitting antenna 20 transmits a RF signal and a receiving antenna 22 receives a RF signal. In this embodiment, both antennas 20 and 22 are disposed within housing 10 and both antennas 20 and 22 are embedded within filter element 16. Although FIG. 1 illustrates antennas 20 and 22 as being embedded in filter element 16, the reader should appreciate that either or both antennas 20 and 22 may be positioned outside filter element 16 and, in some cases, outside housing 10.

Additionally, the term antenna is generically used to describe any radio frequency transmitting and/or receiving device. Furthermore, one skilled in the art would understand that any antenna, including an insertable resonator, could be used for antennae 20 and 22.

Housing 10 may be comprised of a material to insulate transmitting antenna 20 and or receiving antenna 22 from RF noise, which may interfere with system 1 operation.

In at least one embodiment, transmitting antenna 20 and receiving antennae 22 are inserted parallel to the central axis of a cylindrical metal filter housing 10 and are inductively coupled in a direction radial to antennae 20 and 22 and filter 16 axis. These antennae 20 and 22 may be inserted in either end of filter 16 or both in the same end of filter 16. It can be readily demonstrated that the measurement volume is axially confined to the area of overlap of antennae 20 and 22 and in the radial direction by the metal walls of filter 16 housing 10.

Furthermore, each antenna 20 and 22 may consist of one or more metallic elements. The addition of more than one element to an antenna 20 and 22 may be desirable in some applications in order to improve the broadband frequency transmission and reception characteristics of the system 1. System 1 design geometry is closely coupled to the geometry of filter 16. That is, the antenna geometry is adjusted to optimize transmission and reception of a selected frequency range within a specific filter 16 system 1 geometry.

A wide-band frequency source 26 generates source signal 52 and applies source signal 52 to a splitter 28. Splitter 28 applies source signal 52 to both circulator 35 and first detector 30. First detector 30 produces a reference output signal 48 that is representative of the power of source signal 52 prior to transmission.

As mentioned, wide-band frequency source 26 supplies source signal 52 to splitter 28, which sends a reference sample signal 48 of source signal 52 to first detector 30. The remainder of source signal 52 is passed through circulator 35 to transmitting antenna 20, which, in this exemplary embodiment, is inserted into ceramic filter 16. Depending on antenna design, the frequency of source signal 52, and the combined dielectric properties of the filter and soot, some of the RF power of signal 52 is reflected back to circulator 35. In this embodiment, circulator 35 is a directional coupler and the reflected power signal 46 is directed to a second detector 36. Reflected power signal 46 to detector 36 is then sent to first comparator 34. First comparator 34 compares reflected power 46 to reference source power signal 48, which was sent to comparator 34 from detector 30. The ratio of reflected power signal 46 to reference source signal 48 provides a relative measurement of the power reflected 42 by the combined dielectric characteristics (i.e., the effective dielectric constant) of filter 16 and the soot collected therein.

Similarly, the RF power from source signal 52 that is transmitted by antenna 20 and through filter 16 and the soot collected therein is measured by receiving antenna 22 and signal detector 32. This signal 44 is sent to second comparator 37, which compares the transmitted RF power signal 44 to reference power signal 48 from first detector 30. The relative transmitted power signal thus measured is a unique function of the frequency of the transmitted power, antennae 20 and 22 design, and the dielectric properties of filter 16 and the soot collected therein. The strength of this latter signal at any frequency is equal to the relative strength of the source RF signal 52 minus the sum of the reflected RF power signal 46 (a function of the effective dielectric constant) and the amount of adsorbed RF power (a function of the effective dielectric loss factor).

Accordingly, first comparator 37 output signal 40 is representative of the transmission loss through filter medium 16, which, in turn, is representative of the change in the effective dielectric constant and loss factor caused by accumulation of soot within filter 16. It will be seen therefore that when there is little or no accumulation in filter 16, there will be only a small transmission loss in source signal 52 strength. As the soot accumulation increases within filter 16, the difference in signal strength between source signal 52 and transmitted signal 44 changes, resulting in output signal 40 from second comparator 37. Second comparator 37 can be designed to drive a variable output display or an indication when a predetermined level is reached, or both.

The power source is arranged to emit RF energy over a range of frequencies. It can be shown that the complex permittivity of some materials is a function of frequency; hence this latter information can be used in correlations to differentiate the relative quantity of various materials collected within the filter. Other advantages may include the ability to average over a frequency range to reduce the impact of any frequency shift in the source signal. In at least one embodiment, an appropriate frequency band is 200–400 MHz.

INDUSTRIAL APPLICABILITY

Soot from engines, such as an internal combustion diesel engine, is generally composed of a mixture of carbon particles and condensed organic material. The condensed organic material may come from unburned fuel and or lube oil, for example.

Of the mixture, carbon has a relatively high dielectric loss factor. As a result of carbon's relatively high dielectric loss factor, carbon particulate matter is generally a very good absorber of RF energy. The condensed organic material, on the other hand, is generally not a good absorber of RF energy.

Like the condensed organic material, ceramic filters—which are commonly used as particulate filters in engine exhaust systems—are also poor absorbers of RF energy.

Figure 2:
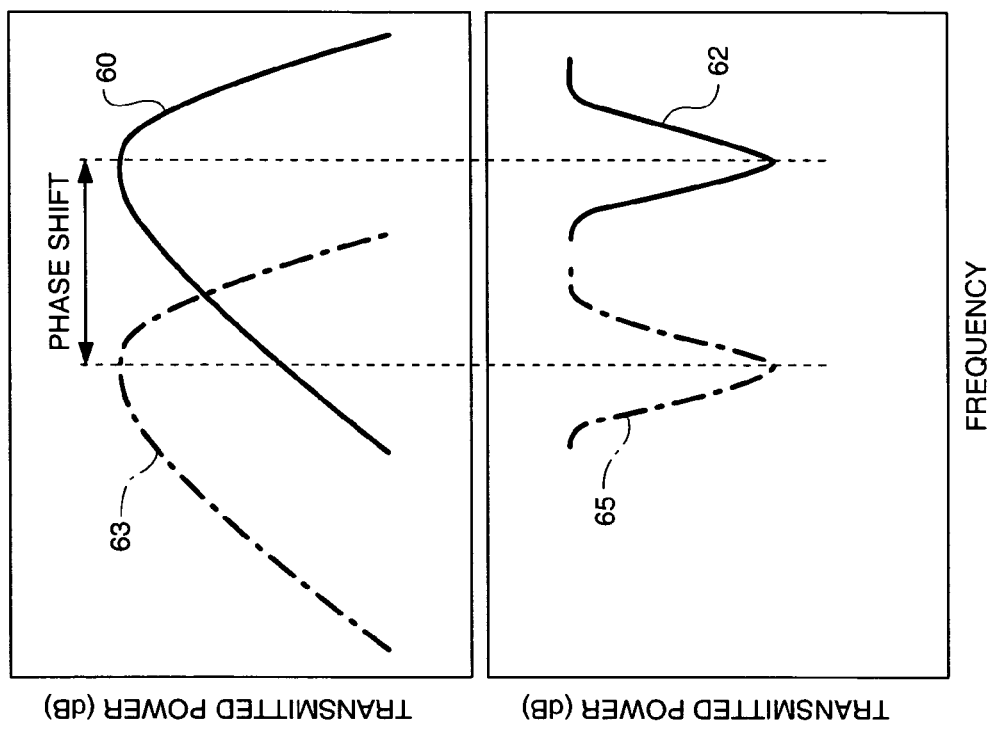
FIG. 2 is a graph illustrating reflected signal strength and transmitted signal strength over a range of frequencies for both a soot-loaded filter and soot-free filter.
Figure 3:
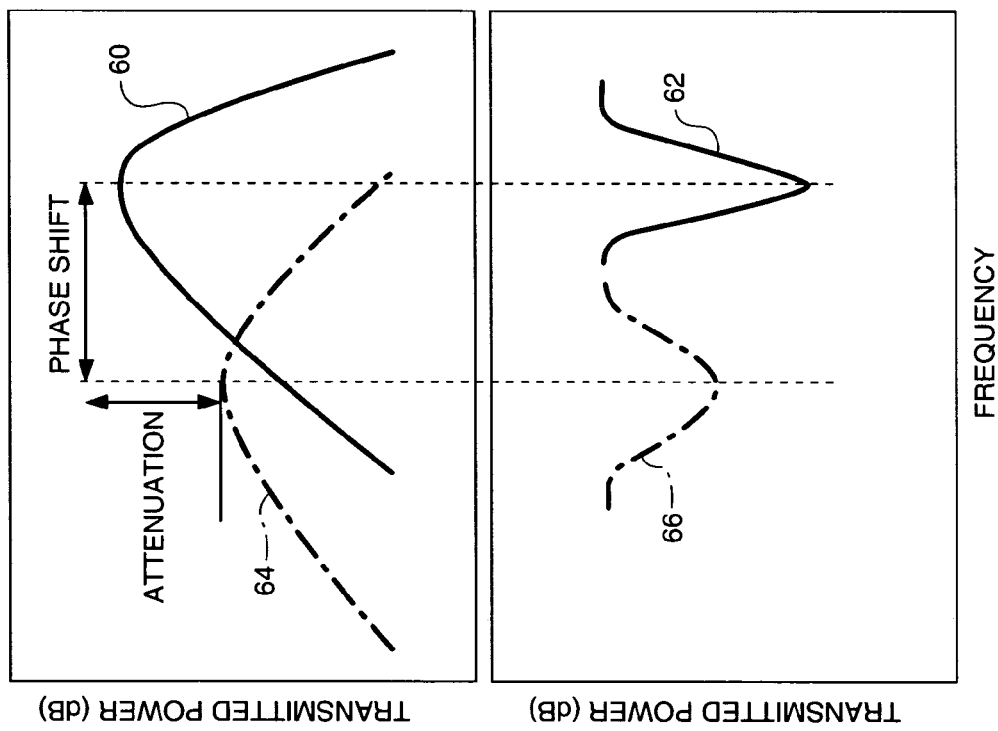
FIG. 3 is a graph illustrating reflected signal strength and transmitted signal strength over a range of frequencies for both a soot-loaded filter with carbon particles and soot-free filter.

FIGS. 2 and 3 depict reflected signals 46 and transmitted signals 44 of FIG. 1 over a range of frequencies. In at least one embodiment, this range of frequencies is from about 200–400 MHz.

If filter 16 is free from carbon particles and condensed organic material, a transmitted signal 60 and reflected signal 62 are generated. These signals 60 and 62 are depicted to illustrate the relative attenuation and phase shifting that occurs when filter 16 is loaded with soot or other material.

Depending on the amount of soot present and the relative amount of carbon particles and condensed organic material, a unique shift in frequency to the relative transmitted signal 44 and reflected signal 46 occurs. As depicted in FIG. 2, if materials collected in filter 16 have low loss factors, then the increase in the effective dielectric constant of the loaded filter 16 would cause a phase shift in frequency. As shown in FIG. 2, a transmitted signal 63 and reflected signal 65 are generated in the soot-loaded filter 16. As can be seen, both signals 63 and 65 are shifted to a lower frequency range, as compared to signals 60 and 62, respectively.

In addition to undergoing a phase shift, transmitted signal 60 may also undergo attenuation, thus resulting in a weakened signal strength. As depicted in FIG. 3, if a material with a high RF absorption capability is collected in filter 16, such as carbon particles, then the transmitted signal 44 is also attenuated. The phase-shifted and attenuated transmitted signal 64 and phase-shifted reflected signal 66 can be compared with non-attenuated and non-phase-shifter signal 60 and on-phase-shifted reflected signal 62, both of which would be measured in a soot-free filter 16.

There is, therefore, a combination of both phase shift and signal attenuation as soot with carbon particulates is collected. These changes in the RF reflected and transmitted relative power spectra can be correlated with calibration data to determine both the amount of soot and the ratio of carbon particulates to condensed organic material present in filter 16. Knowing the amount of soot present as well as the ratio of carbon particulates to condensed organic material may then be used to develop filter 16 regeneration control strategy.

Measurements of the complex permittivity of ash as a function of temperature and frequency have shown that generally under conditions where both soot and ash are being filtered from an engine exhaust, the amount of ash accumulated is largely undetectable by RF measurements due to the presence of soot, which has high dielectric properties relative to ash. However, at the end of the filter regeneration cycle when the soot has been oxidized and the clean filter remains hot, the higher temperatures increase the ash loss factor and the ability to detect the amount of ash present is greatly enhanced. A combination of phase shift and signal attenuation can, therefore, be used to differentiate between a hot, clean ceramic filter and a hot ceramic filter containing accumulated ash. Together with calibration data correlations can, therefore, be developed to assess the quantity of ash present in the filter.

What is claimed is:

1. A method for detecting soot and or ash loading within a diesel particulate filter, comprising:
    transmitting a source RF signal through a diesel particulate filter;
    measuring a reflected RF signal;
    measuring a transmitted RF signal;
    calculating reflected power by comparing the source RF signal with the reflected RF signal;
    calculating attenuated power by comparing the source RF signal with the transmitted RF signal; and
    determining soot loading based on reflected power and transmitted power.

2. The method of claim 1, characterized in that the source RF signal is transmitted over a range of frequencies.

3. The method of claim 2, further characterized in that the range of frequencies is from about 200 MHz to about 400 MHz.

4. The method of claim 1, further comprising the step of determining the ratio of carbon particulates to condensed organic material.

5. The method of claim 1, further comprising the step of determining carbon particulate loading.

6. The method of claim 1, further comprising the step of determining ash loading.

7. A system for measuring soot and or ash loading within a filter, comprising:
    a transmitting antenna configured to transmit a range of radio frequencies across the filter;
    a receiving antenna configured to receive a range of radio frequencies across the filter;
    a first detector configured to receive and send a reference signal;
    a second detector configured to receive and send a reflected signal;
    a third detector configured to receive and send a transmitted signal
    a first comparator configured to compare the reference signal with the reflected signal;
    a second comparator configured to compare the reference signal with the transmitted signal; and
    a controller configured to calculate carbon particulate loading in the filter based on outputs from the first comparator and second comparator.

8. The system of claim 7, characterized in that the transmitting antenna is substantially parallel to the receiving antenna.

9. The system of claim 7, characterized in that the transmitting antenna is imbedded in the filter.

10. The system of claim 7, characterized in that the receiving antenna is imbedded in the filter.

11. The system of claim 7, characterized in that the transmitting antenna is configured to transmit a radio frequency in the range from about 200 MHz to about 400 MHz.

12. The system of claim 7, characterized in that the transmitting antenna is substantially parallel to an axis of the filter.

13. The system of claim 7, characterized in that the receiving antenna is substantially parallel to an axis of the filter.

14. The system of claim 7, comprising a housing configured to shield the receiving antenna and transmitting antenna from RF noise.

15. The system of claim 7, further comprising a controller configured to calculate a ratio of carbon particulates to condensed organic material based on outputs from the first comparator and second comparator.

16. The system of claim 7, further comprising a controller configured to calculate ash loading in the filter based on outputs from the first comparator and second comparator.

17. A method of regenerating a filter, comprising:
    providing the system of claim 7;
    transmitting a range of radio frequencies across the filter with the transmitting antenna;
    receiving a range of radio frequencies across the filter with the receiving antenna;
    receiving and sending the reflected signal to the first comparator;
    receiving and sending the referenced signal to the first comparator and the second comparator;
    receiving and sending the received signal to the second comparator;
    comparing the reference signal with the reflected signal with the first comparator and generating a first signal;
    comparing the reference signal with the received signal with the second comparator and generating a second signal; and
    regenerating the filter based on the first signal and the second signal.

18. A method of controlling regeneration across a diesel particulate filter, comprising:
    providing the system of claim 7;
    transmitting a radio frequency across the diesel particulate filter;
    measuring a reflected signal;
    measuring a signal transmitted through the diesel particulate filter; and
    generating a signal for diesel particulate filter regeneration based on the reflected and the transmitted signal.

19. The method of claim 18, characterized in that the radio frequency is a variable frequency that ranges from about 200 MHz to about 400 MHz.

20. The method of claim 18, further comprising the step of determining the ratio of carbon particulates to condensed organic material.

21. The method of claim 18, further comprising the step of determining carbon particulate loading.

22. The method of claim 18, further comprising the step of determining ash accumulation in the diesel particulate filter.

23. The system in claim 7, in which the filter is a diesel particulate filter.

* * * * *